(12) United States Patent
Nakanishi

(10) Patent No.: US 12,611,472 B2
(45) Date of Patent: Apr. 28, 2026

(54) PRODUCTION METHOD FOR HIGH-PRESSURE PROCESSED MULTILAYER STRUCTURE, AND HIGH-PRESSURE PROCESSING METHOD FOR MULTILAYER STRUCTURE

(71) Applicant: Mitsubishi Chemical Corporation, Tokyo (JP)

(72) Inventor: Shinji Nakanishi, Tokyo (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 123 days.

(21) Appl. No.: 17/579,034

(22) Filed: Jan. 19, 2022

(65) Prior Publication Data

US 2022/0133921 A1     May 5, 2022

Related U.S. Application Data

(63) Continuation of application No. PCT/JP2020/030361, filed on Aug. 7, 2020.

(30) Foreign Application Priority Data

Aug. 9, 2019     (JP) ................................. 2019-146939

(51) Int. Cl.
  *B32B 38/16*          (2006.01)
  *A61L 2/07*           (2006.01)
        (Continued)

(52) U.S. Cl.
  CPC ............ *A61L 2/07* (2013.01); *B32B 38/0036* (2013.01); *B32B 38/162* (2013.01); *B32B 27/306* (2013.01);
        (Continued)

(58) Field of Classification Search
  CPC . B32B 38/0036; B32B 38/162; B32B 27/325; B32B 37/10; B32B 7/12; B32B 7/02; B32B 27/08; B32B 2307/7244; B32B 2250/05; B32B 2439/70; B32B 2250/246; B32B 2250/02; B32B 2309/00; B32B 2307/732; B32B 2307/7242;
        (Continued)

(56) References Cited

FOREIGN PATENT DOCUMENTS

JP     H3-290175     12/1991
JP     H4-148653     5/1992
        (Continued)

OTHER PUBLICATIONS

ESR for EP App. No. 20 851 568.4, dated Aug. 10, 2022.
        (Continued)

*Primary Examiner* — Monica A Huson
(74) *Attorney, Agent, or Firm* — GREENBLUM & BERNSTEIN, P.L.C.

(57)          ABSTRACT

A production method for a high-pressure processed multilayer structure to be used for packages for foods and the like is provided. The production method includes: preparing a multilayer structure including an ethylene-vinyl alcohol copolymer (EVOH) layer formed from a resin composition containing an ethylene-vinyl alcohol copolymer having a saponification degree of greater than 99.7 mol % as a main component and an olefin resin layer having a thickness of less than 100 μm; and high-pressure processing the multilayer structure under a pressure of not lower than 200 MPa in an atmosphere at not lower than 20° C.

4 Claims, 1 Drawing Sheet

(51) Int. Cl.
B32B 38/00 (2006.01)
*B32B 27/30* (2006.01)
*B32B 27/32* (2006.01)

(52) U.S. Cl.
CPC ....... *B32B 27/32* (2013.01); *B32B 2307/7242* (2013.01); *B32B 2307/732* (2013.01); *B32B 2439/70* (2013.01)

(58) Field of Classification Search
CPC ............ B32B 2439/46; B32B 2309/12; B32B 2439/80; B32B 2250/40; B32B 27/32; B32B 27/306; A61L 2/07
See application file for complete search history.

(56) References Cited

FOREIGN PATENT DOCUMENTS

| | | |
|---|---|---|
| JP | H5-69519 A | 3/1993 |
| JP | H10-306180 A | 11/1998 |
| JP | 2012-224844 A | 11/2012 |
| JP | 2016-7754 A | 1/2016 |
| JP | 2016-112883 A | 6/2016 |
| JP | 2018-58298 | 4/2018 |

OTHER PUBLICATIONS

ISR for PCT/JP2020/030361, dated Oct. 20, 2020.
IPRP for PCT/JP2020/030361, dated Feb. 17, 2022 (translation only).
Lopez-Rubio et al., "Effect of high pressure treatments on the properties of EVOH-based food packaging materials", Innovative Food Science and Emerging Technologies, 6:51-58 (2005).
Office Action for JP App. No. 2021-539269, dated Nov. 7, 2023 (w/ translation).
Office Action for CN App. No. 202080052695.1, dated Mar. 28, 2024 (w/ translation).
Office Action for CN App. No. 202080052695.1, dated Sep. 20, 2024 (w/ translation).
Office Action for EP App. No. 20 851 568.4, dated Jul. 24, 2024.
Office Action for JP App. No. 2021-539269, dated May 28, 2024 (w/ translation).
Office Action for CN App. No. 202080052695.1, dated Feb. 24, 2025 (w/ translation).

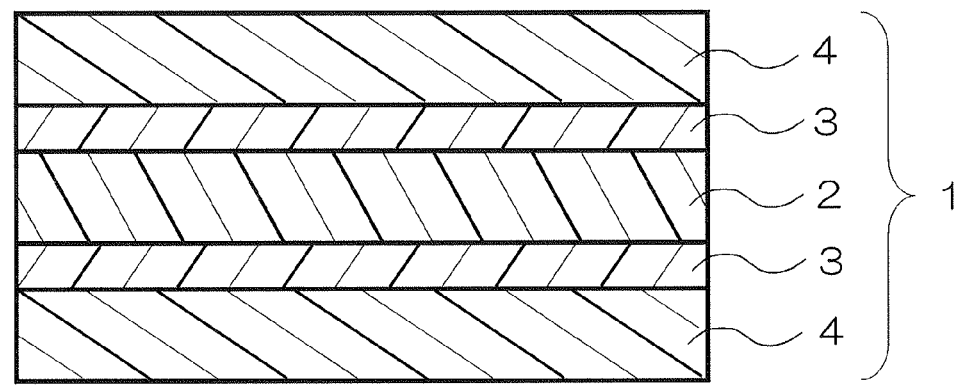

PRODUCTION METHOD FOR HIGH-PRESSURE PROCESSED MULTILAYER STRUCTURE, AND HIGH-PRESSURE PROCESSING METHOD FOR MULTILAYER STRUCTURE

RELATED APPLICATIONS

This application is a continuation of International Application No. PCT/JP2020/030361, filed on Aug. 7, 2020, which claims priority to Japanese Patent Application No. 2019-146939, filed on Aug. 9, 2019, the entire contents of each of which being herein incorporated by reference.

TECHNICAL FIELD

The present disclosure relates to a production method for a high-pressure processed multilayer structure, and to a high-pressure processing method for a multilayer structure including an ethylene-vinyl alcohol copolymer layer and an olefin resin layer.

BACKGROUND ART

In recent years, film packages (multilayer structures having a plurality of layers), which are light-weighted and excellent in post-use volume reduction property as compared with bottles and cans, are used as packages for foods and the like. The multilayer structures are required to have tear resistance and other physical properties with higher strength and higher rigidity and, in addition, higher gas barrier properties for prevention of deterioration of the contents.

On the other hand, the contents packaged with the multilayer structures are generally required to be sterilized together with the multilayer structures from the viewpoint of cleanliness and preservation. Known sterilization methods include hot water treatment processes such as retort process and boiling process, irradiation processes such as irradiation with ultraviolet radiation and gamma radiation, and high-pressure processing processes. Particularly, the high-pressure processing processes are widely employed, because the contents are substantially free from deterioration.

An exemplary high-pressure processing process is disclosed in PTL 1, in which a multilayer structure including a layer of an ethylene-vinyl alcohol copolymer (hereinafter sometimes referred to as "EVOH") having a saponification degree of not less than 95 mol % is high-pressure processed. Further, NPTL 1 discloses a high-pressure processing process, in which a multilayer structure including three layers of polypropylene (hereinafter sometimes referred to as "PP") layer/EVOH layer/PP layer is high-pressure processed.

RELATED ART DOCUMENTS

Patent Document

PTL 1: JP-A-HEI3(1991)-290175

Non-Patent Document

NPTL 1: Amparo Lopez-Rubio, Jose M. Lagaron, Pilar Hernandez-Munoz, Eva Almenar, Ramon Catala, Rafael Gavara, Melvin A. Pascall, Innovative Food Science and Emerging Technologies 6 (2005) 51-58.

SUMMARY

However, it was found that, in the high-pressure processing process disclosed in PTL 1, the content sterilization effect can be provided, but the EVOH layer absorbs moisture, problematically deteriorating the gas barrier property of the multilayer structure. In the process disclosed in NPTL 1, the content sterilization effect can be provided, but the gas barrier property is deteriorated. Therefore, there was no high-pressure processing process capable of improving the gas barrier property.

In view of the foregoing, the present disclosure provides a high-pressure processing method for a multilayer structure including an olefin resin layer and an EVOH layer, and a production method for a high-pressure processed multilayer structure. The multilayer structures are usable for packages for foods and the like, and are improved in gas barrier property by the high-pressure processing.

In view of the foregoing, the inventor conducted intensive studies and, as a result, found that, where a multilayer structure including an EVOH layer formed from a resin composition mainly containing an EVOH having a higher saponification degree and an olefin resin layer having a thickness less than a predetermined thickness level is high-pressure processed under a pressure of not lower than 200 MPa in an atmosphere at a temperature not lower than a predetermined temperature level, the gas barrier property of the multilayer structure can be improved.

To solve the aforementioned problem, the present disclosure has the following features [1] to [4]:

[1] A production method for a high-pressure processed multilayer structure having an EVOH layer and an olefin resin layer, the method including the steps of: preparing a multilayer structure including an EVOH layer formed from a resin composition containing an EVOH having a saponification degree of greater than 99.7 mol % as a main component and an olefin resin layer having a thickness of less than 100 μm; and high-pressure processing the multilayer structure under a pressure of not lower than 200 MPa in an atmosphere at not lower than 20° C.

[2] In the production method for the high-pressure processed multilayer structure according to the feature [1], the high-pressure processing is performed for not shorter than 3 minutes.

[3] A high-pressure processing method for a multilayer structure having an EVOH layer and an olefin resin layer, the EVOH layer being formed from a resin composition containing an EVOH having a saponification degree of greater than 99.7 mol % as a main component, the olefin resin layer having a thickness of less than 100 μm, the method including the step of high-pressure processing the multilayer structure under a pressure of not lower than 200 MPa in an atmosphere at not lower than 20° C.

[4] In the high-pressure processing method for the multilayer structure according to the feature [3], the high-pressure processing is performed for not shorter than 3 minutes.

The multilayer structure high-pressure processing method according to the present disclosure is the high-pressure processing method for the multilayer structure having the EVOH layer and the olefin resin layer. The EVOH layer is formed from the resin composition containing the EVOH having a saponification degree of greater than 99.7 mol % as the main component, and the thickness of the olefin resin layer is less than 100 μm. In the method, the multilayer structure is high-pressure processed under a pressure of not lower than 200 MPa in the atmosphere at not lower than 20° C. Therefore, the multilayer structure has an improved gas barrier property even if being subjected to the high-pressure processing.

The gas barrier property of the multilayer structure can be improved supposedly because the amorphous portion of the EVOH in the EVOH layer is compressed by the high-pressure processing, whereby a lamellar structure having a long-periodic arrangement in the EVOH is regularly folded to increase the crystallinity of the EVOH.

If an EVOH having a lower saponification degree is used, acetyl groups are present at random in the polymer, and steric hindrance is liable to occur due to molecular chains when the amorphous portion of the EVOH is compressed in the high-pressure processing. This supposedly makes it difficult to increase the crystallinity of the EVOH and hence to improve the gas barrier property. Therefore, the gas barrier property is supposedly improved particularly with the use of the EVOH having a higher saponification degree.

In the high-pressure processed multilayer structure production method according to the present disclosure, the multilayer structure is prepared, and high-pressure processed under a pressure of not lower than 200 MPa in the atmosphere at not lower than 20° C. Thus, the multilayer structure can be produced as having an improved gas barrier property.

BRIEF DESCRIPTION OF DRAWING

The FIGURE is a diagram schematically showing a cross section of a multilayer structure to be employed in an embodiment of the present disclosure.

DESCRIPTION OF EMBODIMENTS

Embodiments of the present disclosure will hereinafter be described, but it should be understood that the disclosure be not limited to these embodiments.

According to one embodiment of the present disclosure, a multilayer structure high-pressure processing method is performed on a multilayer structure having at least an olefin resin layer and an EVOH layer. The olefin resin layer has a thickness of less than 100 μm, and the EVOH layer is formed from a resin composition containing an EVOH having a saponification degree of greater than 99.7 mol % as a main component. The multilayer structure is high-pressure processed under a pressure of not lower than 200 MPa in an atmosphere at not lower than 20° C.

According to another embodiment of the present disclosure, a production method for a high-pressure processed multilayer structure includes the steps of: preparing the multilayer structure; and high-pressure processing the multilayer structure under a pressure of not lower than 200 MPa in an atmosphere at not lower than 20° C.

The multilayer structure to be employed in the present disclosure will first be described, and then the high-pressure processing method for the multilayer structure and the production method for the high-pressure processed multilayer structure according to the embodiments of the present disclosure will be described.

[Multilayer Structure]

The FIGURE schematically illustrates a multilayer structure 1 to be employed in the embodiments of the present disclosure. The multilayer structure 1 has a five-layer structure including an EVOH layer 2 and olefin resin layers 4 provided on front and back surfaces of the EVOH layer 2 with the intervention of adhesive resin layers 3. The multilayer structure 1 can be used for various packages, for example, for general foods, condiments such as mayonnaise and dressing, fermented foods such as miso, fat and oil such as salad oil, beverages, cosmetics, pharmaceutical products, and the like. In the FIGURE, each part is schematically illustrated as having dimensions (thickness) different from the actual dimensions.

<EVOH Layer 2>

The EVOH layer 2 mainly serves for the gas barrier property, and is formed from the resin composition containing the EVOH having a saponification degree of greater than 99.7 mol % as the main component. The term "main component" herein means a component that affects the characteristic properties of the material, and is typically present in a proportion of not less than 50 mass % of the entire material, and encompasses a component that is present in a proportion of 100 mass % (the EVOH having a saponification degree of greater than 99.7 mol % is present alone).

The saponification degree of the EVOH is determined based on the vinyl ester content of the EVOH measured in conformity with JIS K6726 (with the use of a solution obtained by homogenously dissolving the EVOH in a water/methanol solvent). The saponification degree of the EVOH is preferably 99.8 to 100 mol %, more preferably 99.9 to 100 mol %. If the saponification degree is excessively low, the gas barrier property tends to be insufficient The EVOH is a resin typically prepared by saponifying a copolymer of ethylene and a vinyl ester monomer (ethylene-vinyl ester copolymer), and is a water-insoluble thermoplastic resin. In the production of the copolymer, a known polymerization method such as solution polymerization method, suspension polymerization method or emulsion polymerization method may be utilized for polymerization of ethylene and the vinyl ester monomer. In general, a solution polymerization method using a lower alcohol (e.g., methanol) as a solvent is utilized. The saponification of the copolymer may be achieved by a known method. The EVOH thus prepared mainly contains an ethylene structural unit and a vinyl alcohol structural unit, and generally further contains a small amount of a vinyl ester structural unit left unsaponified.

Vinyl acetate is preferably used as the vinyl ester monomer, because it is easily commercially available and ensures a higher impurity treatment efficiency in the production. Other examples of the vinyl ester monomer include aliphatic vinyl esters such as vinyl formate, vinyl propionate, vinyl valerate, vinyl butyrate, vinyl isobutyrate, vinyl pivalate, vinyl caprate, vinyl laurate, vinyl stearate, and vinyl versatate, and aromatic vinyl esters such as vinyl benzoate. The aliphatic vinyl esters typically have a carbon number of 3 to 20, preferably 4 to 10, particularly preferably 4 to 7. These may be used alone or in combination.

The ethylene content of the EVOH is preferably 20 to 60 mol %, more preferably 25 to 50 mol %, particularly preferably 25 to 35 mol %, as measured based on ISO 14663. If the ethylene content is excessively low, the high-humidity gas barrier property and the melt formability tend to be deteriorated. If the ethylene content is excessively high, on the other hand, the gas barrier property tends to be deteriorated.

The EVOH preferably has a melt flow rate (MFR) of 0.5 to 100 g/10 minutes, more preferably 1 to 50 g/10 minutes, particularly preferably 3 to 35 g/10 minutes (as measured at 210° C. with a load of 2,160 g). If the MFR is excessively high, the film formability tends to be deteriorated. If the MFR is excessively low, the melt viscosity tends to be excessively increased, making the melt extrusion difficult.

The EVOH may further contain a structural unit derived from any of the following comonomers in addition to the ethylene structural unit and the vinyl alcohol structural unit (and the unsaponified vinyl ester structural unit). The comonomers include: α-olefins such as propylene, isobutene, α-octene, α-dodecene, and α-octadecene, hydroxyl-containing α-olefins such as 3-buten-1-ol, 4-penten-1-ol, and 3-butene-1,2-diol, and derivatives including esterification products and acylation products of these hydroxyl-containing α-olefins; unsaturated carboxylic acids, and salts, partial alkyl esters, full alkyl esters, nitriles, amides, and anhydrides of the unsaturated carboxylic acids; unsaturated sulfonic acids and salts thereof; and vinylsilane compounds, vinyl chloride, and styrene.

Post-modified EVOH resins such as urethanized EVOH, acetalized EVOH, cyanoethylated EVOH, and oxyalkylenated EVOH are also usable as the EVOH. Of these modified EVOH resins, an EVOH having a primary hydroxyl group introduced into its side chain by copolymerization is preferred because the secondary formability is improved in stretching process, vacuum pressure forming process, and the like. Particularly, an EVOH having a 1,2-diol structure in its side chain is preferably used.

The resin composition containing the EVOH as the main component may further contain additives that are generally blended in resin compositions mainly containing the EVOH, as long as the effects of the present disclosure are not impaired. Examples of the additives include heat stabilizer, antioxidant, antistatic agent, colorant, UV absorber, lubricant, plasticizer, light stabilizer, surfactant, antibacterial agent, desiccant, antiblocking agent, flame retarder, crosslinking agent, curing agent, foaming agent, crystal nucleating agent, antifogging agent, biodegradation additive, silane coupling agent, and oxygen absorber. These may be used alone or in combination.

Examples of the heat stabilizer to be used for improving the heat stability and other various physical properties during the melt forming include: organic acids such as acetic acid, propionic acid, butyric acid, lauric acid, stearic acid, oleic acid, and behenic acid, and salts of the organic acids such as alkali metal salts (sodium salts, potassium salts, and the like), alkaline earth metal salts (calcium salts, magnesium salts, and the like), and zinc salts of the organic acids; and inorganic acids such as sulfuric acid, sulfurous acid, carbonic acid, phosphoric acid, and boric acid, and alkali metal salts (sodium salts, potassium salts, and the like), alkaline earth metal salts (calcium salts, magnesium salts, and the like), and zinc salts of the inorganic acids.

A single EVOH or two or more EVOHs may be used for the resin composition containing the EVOH as the main component. EVOHs having different ethylene contents, different saponification degrees, different melt flow rates (MFRs) (as measured at 210° C. with a load of 2,160 g), different copolymerization components, and/or different modification degrees (e.g., different 1,2-diol structural unit contents) may be properly selected for use as the two or more EVOHs.

The resin composition containing the EVOH as the main component preferably further contains a polyamide resin. The polyamide resin is capable of forming a network structure with its amide bonds interacting with hydroxyl groups and/or ester groups of the EVOH, preventing the leaching of the EVOH during the high-pressure processing.

Known polyamide resins are usable as the polyamide resin. Examples of the polyamide resin include: homopolymers such as polycapramide (nylon 6), poly-ω-aminoheptanoic acid (nylon 7), poly-ω-aminononanoic acid (nylon 9), polyundecanamide (nylon 11), and polylauryllactam (nylon 12); polyamide copolymer resins including aliphatic polyamide copolymers such as polyethylenediamine adipamide (nylon 26), polytetramethylene adipamide (nylon 46), polyhexamethylene adipamide (nylon 66), polyhexamethylene sebacamide (nylon 610), polyhexamethylene dodecamide (nylon 612), polyoctamethylene adipamide (nylon 86), polydecamethylene adipamide (nylon 108), caprolactam/lauryllactam copolymer (nylon 6/12), caprolactam/ω-aminononanoic acid copolymer (nylon 6/9), caprolactam/hexamethylenediammonium adipate copolymer (nylon 6/66), lauryllactam/hexamethylenediammonium adipate copolymer (nylon 12/66), ethylenediamine adipamide/hexamethylenediammonium adipate copolymer (nylon 26/66), caprolactam/hexamethylenediammonium adipate/hexamethylenediammonium sebacate copolymer (nylon 66/610), and ethyleneammonium adipate/hexamethylenediammonium adipate/hexamethylenediammonium sebacate copolymer (nylon 6/66/610), and aromatic polyamide copolymers such as polyhexamethylene isophthalamide, polyhexamethylene terephthalamide, poly-m-xylylene adipamide, hexamethylene isophthalamide/terephthalamide copolymer, poly-p-phenylene terephthalamide, and poly-p-phenylene/3,4'-diphenyl ether terephthalamide; and amorphous polyamide, and terminal-modified polyamide resins obtained by terminal-modifying any of these polyamide resins with a carboxyl group or an amino group of methylenebenzylamine or m-xylenediamine. The polyamide copolymer resins are preferred because the gas barrier property can be further improved. Particularly, the aliphatic polyamide copolymers are preferred. These may be used alone or in combination.

In the resin composition containing the EVOH as the main component, the polyamide resin is preferably present in a proportion of, for example, 1 to 40 mass %, more preferably 5 to 35 mass %, based on the overall mass of the resin composition.

The EVOH layer 2 typically has a thickness of 1 to 30 μm, preferably 3 to 28 μm, still more preferably 5 to 25 μm.

<Adhesive Resin Layers 3>

The adhesive resin layers 3, which are provided to increase the adhesive strength between the EVOH layer 2 and the olefin resin layers 4 to be described later, are formed from a resin composition containing an adhesive resin. A known adhesive resin can be used as the adhesive resin, and may be properly selected according to the types of the resins to be used for the EVOH layer 2 and the olefin resin layers 4. A typical example of the adhesive resin is a carboxyl-containing modified polyolefin polymer prepared by chemically bonding an unsaturated carboxylic acid or its anhydride to a polyolefin resin by an addition reaction, a graft reaction or the like. Examples of the modified polyolefin polymer include polyethylene graft-modified with maleic anhydride, polypropylene graft-modified with maleic anhydride, ethylene-propylene (block and random) copolymer graft-modified with maleic anhydride, ethylene-ethyl acrylate copolymer graft-modified with maleic anhydride, ethylene-vinyl acetate copolymer graft-modified with maleic anhydride, polycycloolefin resin modified with maleic anhydride, and polyolefin resin graft-modified with maleic anhydride. For improvement of the water resistance of the multilayer structure 1, highly hydrophobic adhesive resins are preferred, and the polycycloolefin resin is particularly preferred. These may be used alone or in combination.

The polycycloolefin resin has a lower moisture permeability than the linear aliphatic polyolefins such as polyethylene and polypropylene. Where the polycycloolefin resin is used for the adhesive resin layers 3, therefore, it is possible to suppress moisture intrusion from the outside due to humidity, hot-water sterilization process or the like, and to properly maintain the oxygen permeability of the multilayer structure 1 after the high-pressure processing.

The resin composition containing the adhesive resin may contain the adhesive resin alone, but may further contain conventionally known plasticizer, filler, clay (montmorillonite or the like), colorant, antioxidant, antistatic agent, lubricant, nucleating agent, antiblocking agent, UV absorber, wax, and the like.

The adhesive resin layers 3 each typically have a thickness of 1 to 30 μm, preferably 2 to 20 μm, more preferably 3 to 10 μm.

<Olefin Resin Layers 4>

The olefin resin layers 4, which are provided to further improve the strength and the gas barrier property, are formed from a resin composition containing an olefin resin. The olefin resin may be heat-meltable to be heat-bonded to the other layers. Examples of the olefin resin include polypropylene resin, polyethylene resin, polycycloolefin resin, and unsaturated carboxylic acid-modified polyolefin resins obtained by modifying any of these polyolefin resins. Of these, the polypropylene resin is preferred because it is excellent in heat resistance, hygroscopic property, and solvent resistance. These may be used alone or in combination.

Examples of the polypropylene resin include propylene homopolymer, ethylene-propylene random copolymer, ethylene-propylene block copolymer, and copolymer obtained by copolymerizing propylene and a small amount (1 to 10 mass %) of α-olefin (e.g., 1-butene, 1-hexene, 4-methyl-1-pentene or the like). The propylene homopolymer is preferred because of its excellent recyclability and heat sealability, and low costs. The polypropylene resin preferably has a melting point of not lower than 130° C. for hot-water sterilization process under severer conditions.

The resin composition containing the olefin resin may contain the olefin resin alone, but may further contain conventionally known plasticizer, filler, clay (montmorillonite or the like), colorant, antioxidant, antistatic agent, lubricant, nucleating agent, antiblocking agent, UV absorber, wax, and the like.

The olefin resin layers 4 each typically have a thickness of less than 100 μm, preferably 10 to 90 μm. For improvement of the gas barrier property of the multilayer structure 1, the olefin resin layers 4 each more preferably have a thickness of 20 to 80 μm, still more preferably 30 to 70 μm. Where the multilayer structure includes a plurality of olefin resin layers, at least one of the olefin resin layers may have a thickness of less than 100 μm.

The multilayer structure 1 having the EVOH layer 2, the adhesive resin layers 3, and the olefin resin layers 4 (see the FIGURE) can be produced, for example, by melt-forming method, wet lamination method, dry lamination method, solventless lamination method, extrusion lamination method, coextrusion lamination method, inflation method or the like. Particularly, the melt molding method is preferred from the viewpoint of environmental concerns without the use of a solvent and from the viewpoint of costs without the need for a separate laminating step. A known melt-forming method may be employed, and examples of the melt-forming method include extrusion processes (T-die extrusion, tubular film extrusion, blow-molding, melt-spinning, profile extrusion, and the like), and injection-molding processes. The melt-forming temperature is generally selected from a range of 150° C. to 300° C.

The multilayer structure 1 may be produced by preliminarily preparing a multilayer material including desired layers (e.g., an olefin resin layer 4 and an EVOH layer 2) laminated together, and then laminating another multilayer material or a desired layer on the multilayer material thus prepared. In order to reduce costs required for the laminating, a production method including a smaller number of laminating steps is preferred.

The multilayer structure 1 thus produced may be reheated, and may be uniaxially or biaxially stretched by thermoforming method such as drawing, roll stretching method, pantograph stretching method, inflation stretching method, blow molding method or the like to provide a stretched formed product.

The multilayer structure 1 typically has a thickness of 10 to 600 μm, preferably 50 to 300 μm, more preferably 70 to 280 μm, still more preferably 80 to 260 μm. If the thickness of the multilayer structure 1 is excessively small, the multilayer structure 1 tends to be easily broken due to insufficient strength. If the multilayer structure 1 is excessively great, the flexibility tends to be reduced. Where the multilayer structure 1 is reheated (stretched), the thickness described above is the thickness of the reheated (stretched) formed product (this definition also applies in the following description).

In the multilayer structure 1, the thickness ratio between the olefin resin layer 4 and the EVOH layer 2 (olefin resin layer 4/EVOH layer 2) (if these layers each include a plurality of layers, the thickness ratio between the thinnest one of the olefin resin layers and the thinnest one of the EVOH layers) is typically 0.25/1 to 10/1, preferably 1/1 to 8/1, more preferably 2/1 to 6/1.

In the multilayer structure 1, the thickness ratio between the adhesive resin layer 3 and the EVOH layer 2 (adhesive resin layer 3/EVOH layer 2) (if these layers each include a plurality of layers, the thickness ratio between the thinnest one of the adhesive resin layers and the thinnest one of the EVOH layers) is typically 0.1/1 to 10/1, preferably 0.25/1 to 5/1, more preferably 0.5/1 to 2/1.

In this embodiment, the multilayer structure 1 including five layers, i.e., the olefin resin layer 4, the adhesive resin layer 3, the EVOH layer 2, the adhesive resin layer 3, and the olefin resin layer 4 laminated in this order is used (see the FIGURE). Where the multilayer structure 1 includes at least two layers, i.e., the olefin resin layer 4 and the EVOH layer 2, the present disclosure is not limited to this embodiment. As long as the multilayer structure to be used in the present disclosure includes the at least two layers and the effects of the present disclosure are not impaired, the number of the layers of the multilayer structure is not particularly limited, but the multilayer structure may include an additional layer or may have no adhesive resin layer 3. Where the EVOH layer 2 is provided in adjoining relation to the olefin resin layer 4 with the intervention of the adhesive resin layer 3 as in this embodiment, however, the adhesion between the EVOH layer 2 and the olefin resin layer 4 can be further increased, thereby ensuring a higher gas barrier property. From this viewpoint, it is preferred to provide the adhesive resin layer 3 between the EVOH layer 2 and the olefin resin layer 4.

Exemplary resins for the additional layer include polyester resins such as polyethylene terephthalate and polyethylene naphthalate, polyamide resins such as various nylon resins, polyaramid resins, polypropylene resins, polyethylene resins, polycarbonate resins, polyacetal resins, and fluorine-containing resins. Further, a base film may be used as the additional layer. The additional resin layer preferably has a thickness of 1 to 100 μm, more preferably 5 to 90 μm, particularly preferably 10 to 80 μm, per layer.

In this embodiment, the two olefin resin layers 4, which are formed from the same resin composition and have the same thickness, are provided in the multilayer structure 1. Alternatively, the two olefin resin layers 4 may be formed from different resin compositions, and may have different thicknesses. The same applies to the adhesive resin layers 3.

[Production Method for High-Pressure Processed Multilayer Structure]

In the high-pressure processing to be performed in the present disclosure, for example, the multilayer structure 1 is put under high-pressure conditions with the use of water as a medium, whereby the multilayer structure 1 itself or a content packaged with the multilayer structure (hereinafter sometimes referred to simply as "content") is sterilized. The high-pressure processing, which is performed at a lower temperature for a shorter period of time as compared with the ordinary retort sterilization process, is advantageous in that the color, the flavor, and the nutrient of the content are not impaired. The high-pressure processing is performed on the multilayer structure, thereby providing the high-pressure processed multilayer structure of the present disclosure.

In the present disclosure, the pressure to be employed for the high-pressure processing is not lower than 200 MPa, preferably 200 to 800 MPa, more preferably 500 to 700 MPa. If the pressure is excessively low, the gas barrier property tends to be insufficiently improved. If the pressure is excessively high, on the other hand, a greater load tends to be applied to the apparatus.

The temperature to be employed for the high-pressure processing is not lower than 20° C., preferably 20° C. to 90° C., more preferably 50° C. to 80° C. If the temperature is excessively low, the heat amount tends to be insufficient for controlling the molecular motion of the EVOH, making it difficult to improve the barrier property. If the temperature is excessively high, on the other hand, the water as the pressure medium is liable to suffer from bumping, whereby a greater load tends to be applied to the apparatus.

The high-pressure processing is preferably performed for not shorter than 3 minutes, more preferably 5 to 60 minutes. If the processing period is excessively short, the gas barrier property tends to be insufficiently improved. If the processing period is excessively long, on the other hand, a greater load tends to be applied to the apparatus with the inside of the apparatus kept pressurized for a longer period of time, requiring more frequent replacement of a packing and the like.

The high-pressure processing method according to the present disclosure is advantageous for a multilayer structure 1 to be used for various packages, for example, for general foods, condiments such as mayonnaise and dressing, fermented foods such as miso, fat and oil such as salad oil, beverages, cosmetics, pharmaceutical products, and the like. That is, the high-pressure processing method according to the present disclosure is advantageous in that the multilayer structure 1 is excellent in gas barrier property after the high-pressure processing and minimizes the deterioration of the content.

The high-pressure processed multilayer structure production method according to the present disclosure can provide a high-pressure processed multilayer structure having an enhanced (improved) gas barrier property. Where the high-pressure processed multilayer structure is used for packages for general foods, condiments such as mayonnaise and dressing, fermented foods such as miso, fat and oil such as salad oil, beverages, cosmetics, pharmaceutical products, and other contents, the high-pressure processed multilayer structure is advantageous in that the deterioration of the contents can be minimized.

EXAMPLES

The embodiments of the present disclosure will hereinafter be described more specifically by way of examples. However, it should be understood that the present disclosure be not limited to the following examples within the scope of the present disclosure.

First, the following ingredients were prepared as materials for the respective layers of the multilayer structure.

[EVOH Layer]

No. 1: EVOH having an ethylene structural unit content of 29 mol %, a saponification degree of 99.8 mol %, and a MFR of 4.0 g/10 minutes (as measured at 210° C. with a load of 2,160 g)

No. 2: EVOH having an ethylene structural unit content of 44 mol %, a saponification degree of 99.8 mol %, and a MFR of 4.0 g/10 minutes (as measured at 210° C. with a load of 2,160 g)

No. 3: EVOH having an ethylene structural unit content of 44 mol %, a saponification degree of 98.5 mol %, and a MFR of 4.0 g/10 minutes (as measured at 210° C. with a load of 2,160 g)

[Olefin Resin Layer]

Homopolypropylene (NOVATEC EA7AD available from Japan Polypropylene Corporation)

[Adhesive Resin Layer]

Polypropylene adhesive resin (PLEXAR PX6002 available from Lyondellbasell, Inc.)

Examples 1 to 8 and Comparative Examples 1 to 6

Multilayer structures 1 (see FIGURE) each having a five-layer structure of olefin resin layer 4/adhesive resin layer 3/EVOH layer 2/adhesive resin layer 3/olefin resin layer 4 with layer thicknesses and an EVOH layer resin material shown below in Table 1 were produced through film formation by an extrusion method (T-die extrusion) with the use of the materials for the respective layers.

The multilayer structures 1 thus produced were each high-pressure processed under a hydrostatic pressure with the use of water as a medium under conditions shown in Table 1 by means of a high-pressure processing apparatus (Dr. Chef available from Kobe Steel, Ltd.)

[Gas Barrier Improvement Percentage]

The oxygen permeability (cc/m$^2$·day·atm) of each of the multilayer structures 1 was measured under the following conditions by means of an oxygen permeability measuring apparatus (OX-TRAN 2/21 available from Mocon, Inc.) before and after the aforementioned high-pressure processing. Then, a gas barrier improvement percentage (%) was calculated by putting the resulting measurement values into the following expression. The measurement results and the calculation results are shown below in Table 1.

<Measurement Conditions>

Temperature: 23° C.

Humidity on steam supply side: 90% RH

Humidity on carrier gas side: 50% RH

<Gas Barrier Improvement Percentage (%)>

$$\text{Gas barrier improvement percentage (\%)} = (OP_b - OP_a)/OP_b \times 100$$

wherein $OP_b$ is the oxygen permeability before the high-pressure processing, and $OP_a$ is the oxygen permeability after the high-pressure processing.

apparent to those skilled in the art could be made within the scope of the disclosure.

The multilayer structure high-pressure processing method according to the present disclosure, which improves the gas barrier property of the high-pressure processed multilayer structure, can be advantageously utilized when contents

TABLE 1

| | Multilayer structure | | | Processing conditions | | | Oxygen permeability | | Gas barrier |
| | EVOH layer | | Olefin resin layer | Temperature | Pressure | Period | Before processing | After processing | Improvement percentage |
| | Resin type | Thickness (μm) | Thickness (μm) | (° C.) | (MPa) | (min) | (cc/m²dayatm) | (cc/m²dayatm) | (%) |
|---|---|---|---|---|---|---|---|---|---|
| Example 1 | No. 1 | 10 | 40 | 30 | 600 | 5 | 0.85 | 0.83 | 2.4 |
| Example 2 | No. 1 | 10 | 40 | 80 | 300 | 5 | 0.85 | 0.81 | 4.7 |
| Example 3 | No. 1 | 10 | 40 | 80 | 600 | 5 | 0.85 | 0.82 | 3.5 |
| Example 4 | No. 1 | 10 | 40 | 80 | 600 | 15 | 0.85 | 0.64 | 24.7 |
| Example 5 | No. 2 | 10 | 40 | 30 | 600 | 5 | 4.8 | 4.3 | 10.4 |
| Example 6 | No. 2 | 10 | 40 | 80 | 300 | 5 | 4.8 | 4.1 | 14.6 |
| Example 7 | No. 2 | 10 | 40 | 80 | 600 | 5 | 4.8 | 3.8 | 20.8 |
| Example 8 | No. 2 | 10 | 40 | 80 | 600 | 15 | 4.8 | 3.5 | 27.1 |
| Comparative Example 1 | No. 1 | 10 | 140 | 12 | 600 | 5 | 0.85 | 0.85 | 0 |
| Comparative Example 2 | No. 1 | 10 | 40 | 12 | 600 | 5 | 0.9 | 0.92 | −2.2 |
| Comparative Example 3 | No. 2 | 10 | 40 | 12 | 600 | 5 | 4.88 | 4.89 | −0.2 |
| Comparative Example 4 | No. 1 | 10 | 140 | 80 | 600 | 5 | 0.85 | 0.88 | −3.5 |
| Comparative Example 5 | No. 1 | 10 | 40 | 80 | 100 | 5 | 0.85 | 0.85 | 0 |
| Comparative Example 6 | No. 3 | 10 | 40 | 80 | 600 | 5 | 7.6 | 7.8 | −2.6 |

The above results indicate that the multilayer structures each including an olefin resin layer having a specific thickness and an EVOH layer formed from a resin composition containing a specific EVOH as a main component and high-pressure processed under the specific conditions each had an enhanced (improved) gas barrier property (Examples 1 to 8).

In contrast to Examples 1 to 8 in which the gas barrier properties of the multilayer structures were enhanced (improved), the enhancement (improvement) of the gas barrier properties of the multilayer structures was not observed in Comparative Examples 1 to 6 in which at least one of the aforementioned requirements was not satisfied.

This indicates that the multilayer structure high-pressure processing method according to the present disclosure is very useful for various sterilization processes in which the multilayer structure is used for packages.

In the high-pressure processed multilayer structure production method according to the present disclosure, the high-pressure processed multilayer structure having an improved gas barrier property can be produced by performing the high-pressure processing on the multilayer structure.

While specific forms of the embodiments of the present disclosure have been shown in the aforementioned examples, the examples are merely illustrative but not limitative. It is contemplated that various modifications (foods, beverages, and the like) packaged in packages formed by using the multilayer structure are sterilized together with the packages.

REFERENCE SIGNS LIST

1: MULTILAYER STRUCTURE
2: EVOH LAYER
3: ADHESIVE RESIN LAYER
4: OLEFIN RESIN LAYER

The invention claimed is:

1. A production method for a high-pressure processed multilayer structure having an ethylene-vinyl alcohol copolymer layer and olefin resin layers provided on front and back surfaces of the ethylene-vinyl alcohol copolymer layer, the method comprising:

preparing a multilayer structure including an ethylene-vinyl alcohol copolymer layer formed from a resin composition containing an ethylene-vinyl alcohol copolymer having a saponification degree of greater than 99.7 mol % as a main component and at least one of the olefin resin layers has a thickness of less than 100 μm; and high-pressure processing the multilayer structure under a pressure of not lower than 200 MPa in an atmosphere at not lower than 20° C.,

US 12,611,472 B2

13

14 wherein:

a thickness ratio between the thinnest one of the olefin resin layers and the thinnest ethylene-vinyl alcohol copolymer layer is 1/1 to 10/1, and the olefin resin layers consisting of an olefin resin alone, or the olefin resin and at least one selected from the group consisting of plasticizer, filler, clay, colorant, antioxidant, antistatic agent, lubricant, nucleating agent, antiblocking agent, UV absorber, and wax.

2. The production method for the high-pressure processed multilayer structure according to claim 1, wherein the high-pressure processing is performed for not shorter than 3 minutes.

3. A high-pressure processing method for a multilayer structure having an ethylene-vinyl alcohol copolymer layer and olefin resin layers provided on front and back surfaces of the ethylene-vinyl alcohol copolymer layer, the ethylene-vinyl alcohol copolymer layer being formed from a resin composition containing an ethylene-vinyl alcohol copolymer having a saponification degree of greater than 99.7 mol % as a main component, at least one of the olefin resin layers has a thickness of less than 100 µm, the olefin resin layers consisting of an olefin resin alone, or the olefin resin and at least one selected from the group consisting of plasticizer, filler, clay, colorant, antioxidant, antistatic agent, lubricant, nucleating agent, antiblocking agent, UV absorber, and wax, and the method comprising high-pressure processing the multilayer structure under a pressure of not lower than 200 MPa in an atmosphere at 50 to 80° C.

4. The high-pressure processing method for the multilayer structure according to claim 3, wherein the high-pressure processing is performed for not shorter than 3 minutes.

* * * * *